United States Patent
Zakariaie et al.

(10) Patent No.: US 10,575,728 B2
(45) Date of Patent: Mar. 3, 2020

(54) EMOTIONAL INTELLIGENCE ENGINE VIA THE EYE

(71) Applicant: Senseye, Inc., Austin, TX (US)

(72) Inventors: David Bobbak Zakariaie, Los Angeles, CA (US); Steven Thurman, Anaheim, CA (US); Derrik Asher, Sherman Oaks, CA (US); Jacqueline Parzivand, Los Angeles, CA (US)

(73) Assignee: Senseye, Inc., Austin, TX (US)

( * ) Notice: Subject to any disclaimer, the term of this patent is extended or adjusted under 35 U.S.C. 154(b) by 0 days.

(21) Appl. No.: 15/289,146

(22) Filed: Oct. 8, 2016

(65) Prior Publication Data
US 2017/0100032 A1   Apr. 13, 2017

Related U.S. Application Data

(60) Provisional application No. 62/239,840, filed on Oct. 9, 2015.

(51) Int. Cl.
| | |
|---|---|
| *A61B 3/113* | (2006.01) |
| *A61B 3/14* | (2006.01) |
| *A61B 3/00* | (2006.01) |
| *A61B 3/11* | (2006.01) |
| *A61B 5/11* | (2006.01) |
| *A61B 5/16* | (2006.01) |

(52) U.S. Cl.
CPC ............ *A61B 3/113* (2013.01); *A61B 3/0025* (2013.01); *A61B 3/112* (2013.01); *A61B 3/145* (2013.01); *A61B 5/1103* (2013.01); *A61B 5/165* (2013.01)

(58) Field of Classification Search
CPC ....... A61B 3/113; A61B 3/0025; A61B 3/112; A61B 3/145; A61B 5/1103; A61B 5/165
USPC ................ 351/201–210; 600/558; 396/51
See application file for complete search history.

(56) References Cited

U.S. PATENT DOCUMENTS

| | | | |
|---|---|---|---|
| 2007/0066916 A1* | 3/2007 | Lemos .................. | A61B 3/113 600/558 |
| 2011/0077548 A1* | 3/2011 | Torch .................... | A61B 3/112 600/558 |

(Continued)

OTHER PUBLICATIONS

A.S.D. Spiers, et al., Action of Dopamine on the Human Iris, British Medical Journal, Nov. 8, 1969, pp. 333-335; vol. 4.

(Continued)

*Primary Examiner* — Kristina M Deherrera
(74) *Attorney, Agent, or Firm* — Hackler Daghighian Martino & Novak

(57) ABSTRACT

A method of discovering relationships between eye movements and emotional responses of a user starts with engaging the user in a plurality of tasks configured to elicit a predicted specific emotional response or allowing the user to experience a naturalistic environment with free-form social interactions. A first camera films at least one eye of the user recording a first time series of eye movements and a second camera films an outward looking view of the user recording a second time series of outward events perceived by the user. The first and second time series are sent to a computing device which compares the eye movements from the first time series and the outward events from the second time series. The computing device can then identify at least one relationship between eye movements that correlate to an actual specific emotional response.

22 Claims, 1 Drawing Sheet

(56) References Cited

U.S. PATENT DOCUMENTS

2014/0223462 A1* 8/2014 Aimone ........... H04N 21/42201
  725/10
2016/0100803 A1* 4/2016 Korzinov ........... A61B 5/04012
  600/301

OTHER PUBLICATIONS

Jianhua Tao, et al., Affective Computing: A Review, 2005, pp. 981-995, National Laboratory of Pattern Recognition, Institute of Automation, Chinese Academy of Sciences, Beijing.
J.A. Stern, et al., Blink Rate As a Measure of Fatigue; A Review, Aug. 1994, pp. 1-12, Office of Aviation Medicine, Washington, DC.
Daniel Bruneau, et al., The Eyes Never Lie: the Use of Eye Tracking Data in HCI Research, pp. 1-6, Department of Computer Science, University College London.
Christine N. Smith, et al., Experience-Dependent Eye Movements, Awareness, and Hippocampus-Dependent Memory; The Journal of Neuroscience, Nov. 1, 2006, 26(44), pp. 11304-11312.
Mary Hayhoe, et al., Eye Movements in Natural Behavior, Trends in Cognitive Sciences, vol. 9, No. 4, Apr. 2005, pp. 188-194.
Deborah E. Hannula, et al., Worth a Glance: Using Eye Movements to Investigate the Cognitive Neuroscience of Memory, Frontiers in Human Neuroscience, Oct. 8, 2010, vol. 4, Article 166, pp. 1-16.
Eva Hudlicka, Affective Computing for Game Design, Proceedings of the 4th Intl. North American Conference on Intelligent Games and Simulation, McGill University, Montreal, Canada, 2008, pp. 5-12.
Sarah Shultz, et al., Inhibition of Eye Blinking Reveals Subjective Perceptions of Stimulus Salience, PNAS, Dec. 27, 2011, vol. 108, No. 52, pp. 21270-21275.
Zhe Gan, et al., Learning Deep Sigmoid Belief Networks with Data Augmentation, Department of Electrical and Computer Engineering, Duke University, Durham NC, pp. 1-9.
Simon P. Liversedge et al., Saccadic Eye Movements and Cognition, Tends in Cognitive Sciences, Jan. 2000, vol. 4, No. 1, pp. 6-14.
Hans Strasburger, Peripheral Vision and Pattern Recognition: A Review, Journal of Vision, 2011, 11(5): 13; pp. 1-82.
Tepring Piquado, et al., Pupillometry as a Measure of Cognitive Effort in Younger and Older Adults, Psychophysiology, May 1, 2010, 47(3), pp. 560-569.
Marc Pomplun, et al., Pupil Dilation as an Indicator of Cognitive Workload in Human-Computer Interaction, Department of Computer Science, University of Massachusetts at Boston, pp. 1-5.
Jackson Beatty, et al., Puppillary Changes in Two Memory Tasks, Psychon. Sci., 1966, vol. 5(10), pp. 371-372.
Tadas Baltrusaitis, et al., Real-Time Inference of Mental States from Facial Expressions and Upper Body Gestures, Face and Gesture, 2011, Santa Barbara, CA, pp. 909-914, Institute of Electrical and Electronics Engineers.
Richard S. Sutton, et al., Reinforcement Learning: An Introduction, 2012, pp. 1-320, The MIT Press, Cambridge, Massachusetts.
A G Rosati, et al., Social Cognition: From Behavior-Reading to Mind-Reading, Encyclopedia of Behavioral Neuroscience, 2010, vol. 3, pp. 263-268, Oxford: Academic Press.
Chengyao Shen, et al., Learning to Predict Eye Fixations for Semantic Contents Using Multi-Layer Sparse Network, Neurocomputing 138, 2014, pp. 61-18.
Honglak Lee, et al., Sparse Deep Belief Net Model for Visual Area V2, pp. 1-8, Computer Science Department, Stanford University, Stanford, CA.
Deborah E. Hannula, et al., The Eyes Have It: Hippocampal Activity Predicts Expression of Memory in Eye Movements, Neuron, Sep. 10, 2009, 63(5), pp. 592-599.
Melvyn A. Goodale, Transforming Vision into Action, Vision Research 51, 2011, pp. 1567-1587.

* cited by examiner

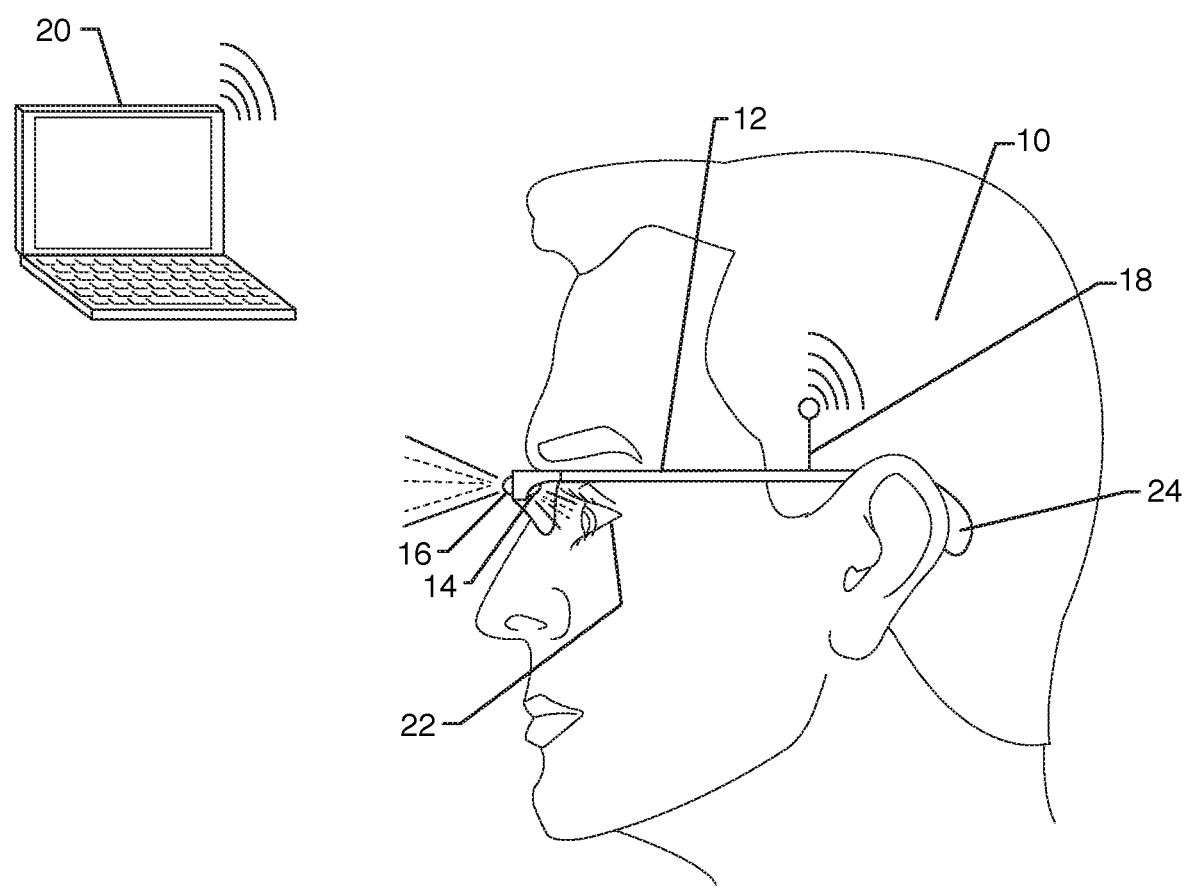

EMOTIONAL INTELLIGENCE ENGINE VIA THE EYE

CROSS-REFERENCE TO RELATED APPLICATIONS

This application claims priority to provisional application 62/239,840 filed on Oct. 9, 2015, the entire contents of which are fully incorporated herein with these references.

DESCRIPTION

Field of the Invention

The present invention is a computational (Bayesian deep belief, neural network, and other machine learning techniques) model that takes in behaviors from the user's eye and adaptively makes real-time accurate inferences about the user's cognitive and emotional states, collectively referred to as mental states. The computational model can interface with any device that will provide the model with a sufficient set of eye behaviors (e.g., pupil dilation, blink rate, blink duration, eye movements, etc.).

Background of the Invention

A key aspect of human social behavior is the ability to mind read (Dunbar, 1998; Rosati & Hare, 2010; Teufel, Fletcher, & Davis, 2010)—essentially the ability to accurately infer the emotional and cognitive states of others on the basis of expressive behaviors. Though humans seem to do this rather effortlessly, mind-reading is a very challenging task, especially for computers, owing to the fact that mental states are contained wholly within the mind of the person and the only data available to an outside observer is the other persons' actions and behaviors. In fact, there are a host of features that are well known to carry information about mental state, including facial expressions (Back, Jordan, & Sharon, 2009; Baltrušaitis et al., 2011; El Kaliouby & Robinson, 2005; Pan, Gillies, Sezgin, & Loscos, 2007), body posture/language (de Gelder, 2006; Kleinsmith & Bianchi-Berthouze, 2007; Mariska E Kret, Stekelenburg, Roelofs, & de Gelder, 2013; Qiu & Helbig, 2012), actions (Gray & Breazeal, 2012; Johnson, Robinson, & Mitchell, 2004), vocalizations (Sauter, Eisner, Ekman, & Scott, 2010; Simon-Thomas, Keltner, Sauter, Sinicropi-Yao, & Abramson, 2009), and eye behaviors (Benedetto et al., 2011; Bruneau, Sasse, & McCarthy, 2002; Hayhoe & Ballard, 2005; Liversedge & Findlay, 2000). There are also physiological changes such as heart rate (Prigatano & Johnson, 1974; Quintana, Guastella, Outhred, Hickie, & Kemp, 2012; Richard Jennings, Allen, Gianaros, Thayer, & Manuck, 2015), pupil dilation (M. E. Kret, Fischer, & De Dreu, 2015; Laeng, Sirois, & Gredeback, 2012; Piquado, Isaacowitz, & Wingfield, 2010), and perspiration (Daniel Kahneman, Tursky, Shapiro, & Crider, 1969; Prigatano & Johnson, 1974) that correlate strongly with mental state and that have been classically used for applications such as lie detection (Brinke, Stimson, & Carney, 2014; Gronau, Ben-Shakhar, & Cohen, 2005) or to determine a person's level of attentional engagement (Driver & Frackowiak, 2001).

In principle, the ability of a computer system to provide accurate inference on human mental states is only limited by its ability to extract the most relevant features from behavior and to essentially decode the message that is contained within the data, similar to social intelligence displayed by humans. Since living humans provide the best known system for breaking the code and inferring mental states, one principle method to this end is to try to mimic human observers in the information they use and the strategies employed in mind-reading. This approach requires careful experimentation with well-controlled social stimuli to determine how humans perform this task and to precisely characterize the pattern of information they use for this purpose. Making machines more like humans to achieve mind-reading is an approach that has been employed by past studies to some degree (Hudlicka, 2008; Peter, Ebert, & Beikirch, 2005; Picard, 1995; Tao & Tan, 2005), but for which there is much more work that needs to be done.

Another approach to solving this problem is to use state-of-the-art machine learning algorithms armed with the capacity to uncover complex structure and patterns in the data that are predictive of a person's mental state. The promise of this approach is that it is more exploratory and therefore has the potential to reveal diagnostic information and strategies that might not be obvious by simply trying to measure the information that humans utilize for this general task. For instance, Bayesian Deep Belief networks (DBN) have found promising applications in a variety of fields such as: universal approximators (Le Roux & Bengio, 2010), autonomous off-road driving (Hadsell, Erkan, Sermanet, Scoffier, & Muller, 2008) flexible memory controllers (Jiang, Hu, & Lujan, 2013), word meaning disambiguation (Wiriyathammabhum & Kijsirikul, 2012), affective/emotional state approximation from electroencephalography (Li, Li, Zhang, & Zhang, 2013), data augmentation (Gan, Henao, Carlson, & Carin, 2015), financial prediction (Ribeiro & Lopes, 2011), modeling physiological data (Wang & Shang, 2013), context dependent behavior (Raudies, Zilli, & Hasselmo, 2014), learning emotion-based acoustic features (E. M. Schmidt & Kim, 2011), traffic flow prediction (Huang, Song, Hong, & Xie, 2014), visual data classification (Liu, Zhou, & Chen, 2011), natural language understanding (Sarikaya, Hinton, & Deoras, 2014), vocalizations (Zhang & Wu, 2013), and modeling brain areas (Lee, Ekanadham, & Ng, 2008) to name a few. DBNs have demonstrated the ability to make reliable inferences on difficult tasks using sparse and noisy multidimensional data structures as input. In vision, DBNs offer a method to build abstract intermediate representations of visual input and to achieve near-human recognition rates for complex global shapes with some invariance to size, viewpoint and local image properties (Shen, Song, & Qi, 2012; Zhou, Chen, & Wang, 2010). Hence, DBNs are capable of solving problems that have historically proven very challenging for artificial systems, much in the same way that the human brain appears to elegantly solve such challenging problems. However, much less prior work has employed state-of-the-art machine learning methods to decode human mental states from observable behavioral data.

A key issue to resolve is to determine what information is most valuable, reliable and informative. Facial expressions are strongly linked to mental states related to emotion (happy, angry, frustrated) and cognition (engaged, bored, contemplating), and therefore provide a relatively strong basis in principle for mind-reading. Yet, one problem with facial expressions is that they are mostly under voluntary control, and hence, can be deceptive or misleading (Gosselin, Perron, & Beaupré, 2010; Matsumoto & Lee, 1993; Recio, Shmuilovich, & Sommer, 2014; K. L. Schmidt, VanSwearingen, & Levenstein, 2005). In other words, there are limitations to the accuracy of mental inference on the basis of facial expression alone. Tonal aspects of how we speak, or voice intonation, also carry information about mental states (Rodero, 2011; Scherer & Sander, 2005; Simon-Thomas et al., 2009). For instance, a person that is sad will have different intonations than a person that is angry. This information has been shown to help distinguish emotional states, but like facial expressions, voice intonation is mostly under cognitive control and have variations across ages and cultures, which contribute to the limited potential of this approach. Body posture and stylistic aspects of human gait also provide insight into mental states (de Gelder, 2006; Kleinsmith & Bianchi-Berthouze, 2007; Mariska E Kret et al., 2013; Qiu & Helbig, 2012), but these approaches to mental state inference face qualitatively similar issues as those faced by facial expressions and vocal tone.

An ideal approach would leverage information that is highly expressive (high signal) and highly correlated to mental states (high validity), and is expressed more universally across people and with less susceptibility to cognitive control and therefore more robust to deception or feigned emotion. Research on human eye behavior suggests that multiple eye features meet all three of these criteria to some degree. Prior work has even had strong success in predicting various mental states from eye data alone (Hayhoe & Ballard, 2005; Holland & Tarlow, 1975; Laeng et al., 2012; Liversedge & Findlay, 2000; Pomplun & Sunkara, 2003; Shultz, Klin, & Jones, 2011; Siegle, Ichikawa, & Steinhauer, 2008). A benefit of measuring eye behavior is that methods are well established and widely available to measure precise features such as gaze location and pupil diameter, owing to the fact that eye-tracking has played such a prominent role in basic psychology research for decades (Gilchrist, Brown, & Findlay, 1997; Rosch & Vogel-Walcutt, 2013). Further, eye data can also be acquired cheaply and non-invasively simply by positioning an infrared video camera near the front of the eye.

The aim of this proposal is to produce a software platform for distinguishing human mental states on the basis of information collected from video images of the eye in naturalistic behavioral settings. The future goal of this work is to create software applications that are adaptive to the emotional needs and mental states of the human user to effectively increase the social intelligence of the artificial system. This will involve basic research and development in several areas to arrive at an accurate and workable system, including development in computer vision to extract relevant eye features from the video, in behavioral experiments to link the extracted eye features to methodologically induced mental states, and in machine learning to produce intelligent probabilistic inferences on mental states from a large set of time series data representing different aspects of eye behavior. These issues are addressed in turn in the following sections as part of the overall research plan.

Linking Eye Behavior to Complex Mental States

The eye has long been thought to provide a window to the soul, or at least to the inner workings of the human mind (Aslin, 2012; Laeng et al., 2012; Lappe, 2008; McCarley & Kramer, 2006; Zekveld, Heslenfeld, Johnsrude, Versfeld, & Kramer, 2014). Research in the field of psychology since the 1960s has indeed revealed that the human eye does provide a sort of direct window to certain aspects of brain function and cognitive processing (Beatty & Kahneman, 1966; Daniel Kahneman et al., 1969). Much of this work has centered on the iris and the pupillary system, because pupil diameter changes constantly and dynamically in response to both changes of lighting in the environment, but also to internal changes in mental state. Early studies by Daniel Kahneman showed compelling links between event related changes in pupil diameter and mental load (Beatty & Kahneman, 1966; Daniel Kahneman et al., 1969; Laeng et al., 2012). In fact, Kahneman is even quoted as saying, "Much like the electricity meter outside your house, the pupils offer an index of the current rate at which mental energy is used".—Task related increases in pupil diameter have also been linked to various functions such as emotional arousal (Bradley, Miccoli, Escrig, & Lang, 2008), memory (Beatty & Kahneman, 1966; Hannula & Ranganath, 2009; D Kahneman & Beatty, 1966; Papesh, Goldinger, & Hout, 2012; C. N. Smith, Hopkins, & Squire, 2006), fatigue (Heishman, Duric, & Wechsler, 2004; Marshall, 2007; Stern, Boyer, & Schroeder, 1994) and attention (Lipp, Siddle, & Dall, 1997; Nieuwenhuis, Gilzenrat, Holmes, & Cohen, 2005; van Steenbergen, Band, & Hommel, 2011; Yu & Dayan, 2005).

The diameter of the pupil is controlled by the push/pull relationship between the sphincter muscles (constriction) and the dilator muscles in the iris (Neuhuber & Schrödl, 2011; Spiers & Caine, 1969; Yoshitomi, Ito, & Inomata, 1985). These two sets of muscles are controlled directly by the two aspects of the autonomic nervous system, where dilator muscles are influenced by the sympathetic branch and sphincter muscles by the parasympathetic branch (Kreibig, 2010). These branches of the autonomic nervous system control fundamental aspects of brain function such as the stress response (e.g. fight or flight) and the counter effective sedative response (e.g. calming or shutting down). These systems modulate peripheral physiological responses mainly via messenger chemicals in the blood stream and via neuromodulation in the brain, where norepinephrine is causally linked to pupil dilation and acetylcholine is linked to pupil constriction (Pintor, 2010). In a genuine sense, the dynamics of pupil dilation and constriction offer a direct window to neuromodulatory systems in the brain (Yoshitomi et al., 1985), and therefore to cognitive and emotional mental states. Importantly, this aspect of eye behavior is controlled non-consciously, suggesting that it provides a relatively faithful representation of mental states without the possibility of deception or voluntary control.

Beyond pupil dilation, which has received the most concerted focus in this field of research, there are other features of eye behavior that link strongly to features such as the focus of attention, level of engagement, experience and depth of learning, task difficulty, and fatigue. In terms of eye blinking, previous work has examined features such as blink rate, latency, and duration (Benedetto et al., 2011; Kamienkowski, Navajas, & Sigman, 2012; Lipp et al., 1997; Schwabe et al., 2011; Stern et al., 1994; Trippe, Hewig, Heydel, Hecht, & Miltner, 2007). The connection between blink rate and certain cognitive states is intuitive, for example, when a person is highly engaged and focused on a task or feature of the environment then blink duration and rate will both typically decrease (MacLean & Arnell, 2011). A person with fatigue will instead have longer blink duration (Stern et al., 1994), and a person with high perceptual load will have a faster blink rate but with a short duration (Holland & Tarlow, 1975). Some applications have used blink rate to detect fatigue in simulated driving conditions (Benedetto et al., 2011), and others have investigated its use in improving adaptive learning modules (S. D. Smith, Most, Newsome, & Zald, 2006).

Gaze behavior has been linked theoretically and experimentally to attentional processes (Hooker et al., 2003), level of interest (Hooker et al., 2003), information processing (Chen & Epps, 2013), vigilance (Marshall, 2007), mental workload (Liversedge & Findlay, 2000), memory retrieval (Hannula et al., 2010) and even personality traits (Rauthmann, Seubert, Sachse, & Furtner, 2012). Our visual system is organized such that we have high acuity and visual processing abilities in the central fovea and the surrounding parafoveal regions of the retina (Goodale, 2011), which spans just a few degrees of the visual field. Visual information is much coarser in the periphery (Strasburger, Rentschler, & Jüttner, 2011), although the periphery does have increased sensitivity to motion, low contrast, and dark environments. As a result, our visual scanning behavior reflects to a great degree the sampling of detailed information from the environment, which is necessary for fine discrimination of features and objects. Hence, where we fixate our eyes is a strong indication of where we think important and relevant information is at each moment in time. Furthermore, eye movements, gaze shifts, or saccades are higher velocity and more numerous under the state of stress or high vigilance and are slower and less numerous when we are concentrating or relaxing (Hayhoe & Ballard, 2005).

While each of these features has been studied in depth and has been related to various aspects of mental processing, most prior work has examined these features in relative isolation. We hypothesize that there is much information to be gained by analyzing these features dynamically and together, rather than as isolated variables. Much like multivoxel pattern analysis in fMRI brain imaging, where patterns of voxel activity are found to carry significant and relevant information about brain processes only when analyzed together as part of a larger system, we anticipate that similar machine learning approaches will provide a very useful framework for discovering information in patterns of eye features to essentially help "break the code" of the working mind. This work will require carefully designed empirical studies to induce specific emotions to be used as labels for supervised learning of a computer model. The next section discusses our plans to apply Bayesian deep learning networks to tackle this issue and the following section will give details of two behavioral experiments we plan to run to provide suitable and reliable training data to the model to discriminate a selection of mental states.

Bayesian Deep Learning Networks:

In general, Deep belief networks (DBNs) or Deep learning (DL) techniques find a causal link between actions and effects, which is why these algorithms have won numerous official international pattern recognition competitions (i.e., Brain Segmentation Contest, Computer Vision Contests, Data Science Competitions, Kaggle Competitions, and others). DL is a branch of machine learning that models high-level abstractions in data by utilizing multiple processing layers with complex structures composed of non-linear transformations, much like Neural Networks (NN) used to model the human brain.

Simple NN-like models have been around for many decades if not centuries. NNs typically have multiple successive nonlinear layers of neurons, and date back at least 50 years (Tadeusiewicz, 1995). The gradient descent method for teacher-based Supervised Learning (SL) is referred to as backpropagation (BP), and was first implemented in the 1960s (Benvenuto & Piazza, 1992). However, due to computational constraints and the lack of general technology development, BP-based training of deep NNs with multiple layers was not practical until the late 1980s. DL became practically feasible to some extent through the help of Unsupervised Learning (UL) (Barlow, 1989). More recently, purely teacher-based supervised DL architectures showed a significant improvement over the unsupervised DL architectures, evidence supported by winning pattern recognition competitions. Deep NNs also have become relevant for the general field of Reinforcement Learning (RL) where there is no supervising teacher and the algorithm adaptively adjusts to the environment/inputs (Sutton & Barto, 1998, 2012).

There are two distinguishable architectures for NNs, feedforward (acyclic) neural networks (FNNs) and recurrent (cyclic) neural networks (RNNs) (Ramazan-Gencay, 1997; Wyatte, Curran, & O'Reilly, 2012). RNNs have been considered the deepest of all NNs because they are more complex and have more processing power than FNNs of the same architecture size (i.e., same number of network nodes and layers) (Dahl, Yu, Deng, & Acero, 2012). Unlike traditional methods for automatic sequential programs (i.e., hard-coded networks), RNNs can learn programs that mix sequential and parallel information processing in a natural and efficient way, exploiting the massive parallelism viewed as crucial for sustaining the rapid decline of computational cost (i.e., time the algorithm takes to process data) observed over the past 75 years.

As stated previously, DBNs have been shown to find causal relationships in data and can modify their own structure (i.e., connections), resulting in an adaptive algorithm that can capture the individual differences inherent in humans (Lopes & Ribeiro, 2014). Our experimental paradigm will explore the different variations of adaptive DBNs in order to uncover the optimal architecture and algorithms that will result in real-time eye feature extraction and mental state inference. The DBN will provide a basis for a "user model", a model that is tailored specifically for decoding the mental states of a particular user. This is achieved after continued use of the software with user feedback on mental states.

SUMMARY OF THE INVENTION

Humans have the capacity to "mind read"—i.e. to make efficient and accurate inferences about the hidden mental states of others. This ability is useful in promoting effective social interactions, empathy and social understanding. With continued advancement of computer technology and its connection to our daily lives, the development of socially intelligent machines is becoming less of a dream and more of an exciting reality. Our research team is dedicated to pushing the boundaries of social computing and neurocognitive monitoring by focusing on the direct relationship that exists between the eye and brain. In fact, decades of research have unveiled the interactive influence of cognition, emotion, and neuromodulatory systems on many aspects of eye behavior, suggesting that the eye truly is a window to the human mind. Our research leverages these causal relationships with modern machine learning algorithms to learn the mapping between eye features and dynamic changes in mental state. Predictive precision is increased by adaptively learning network weights over time to maximize the ability of the user model to infer mental states for each individual person. This Social Intelligence Engine can produce state-of-the-art mind-reading capabilities and will serve as a platform for numerous applications for consumers and professionals in industry.

In the first stage of development, we will create a mobile hardware device comprising an eye-facing near-infrared camera, a world facing HD camera, and various sensors with remote connectivity to any computing device such as a PC, smart phone, or tablet. The device will clip simply and non-invasively onto the frame of generic glasses, and will supply video input of eye data to a remote computer running our software, which uses computer vision algorithms to extract various informative features from the video feed. The time course of these features serves as input to a Bayesian deep belief network (DBN), which is designed to discover complex data patterns and to generate accurate probabilistic interpretations, or inferences, of the user's mental states at each moment in time. Based on our proprietary research, the model will be trained to reliably discriminate several key dimensions, for instance, the continuum from fatigue to vigilance, frustration to satisfaction, boredom to engagement, negative to positive emotional valence, low to high emotional expressivity, and low to high cognitive load. The output of this Social Intelligence Engine will represent a live feed of mental states with actionable information for other software applications.

We envision immediate applications in several domains, such as improving mental health diagnoses and rehabilitation in medicine, creating customizable teaching and learning applications in education, developing emotionally resonant adaptive gaming in entertainment, and supporting innovative methods for data analysis in market research and basic research in psychology and related fields of study. A user friendly device that supplies a live stream of thoughts and feelings as the user interacts with computer software will also provide a ground-breaking platform for app development that could be truly disruptive to the domain of mobile consumer applications. Looking to the future, we anticipate significant uses for this technology in developing emotionally intelligent robotics and, more generally, in fostering a more symbiotic relationship between humans and machines.

In the long term, we are working toward developing a smart contact lens with the capability of recording and supplying eye behavior data directly to a computer running our software. The smart contact lens will have a microscopic DNA computer and molecular sensors on board to support this functionality. In fact, with a patent application in DNA computing and award recognition for this work from the United States Office of Naval Research, our company is well-positioned to be one of the first innovators in this field. Although it may sound too futuristic to some, we aim to change the idea of a mind-reading, contact lens human-computer interface from science fiction to reality. This technology carries the implications and potential to be a total game-changer in the sense that DNA computers will render current silicon based technologies as useful as the cassette tape.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a simplified schematic of the present invention showing a user wearing a pair glasses with an infrared camera aimed as the user's eye and a forward looking camera taking in the environmental view of the user.

DETAILED DESCRIPTION OF THE PREFERRED EMBODIMENTS

The approach involved recording a time series of eye behaviors while the subject engaged in a game or task that was carefully controlled to induce very specific mental (cognitive or emotional) states at particular moments in time. The measured time series of eye behaviors represented the feature set (dependent variables) to serve as input to the model, while the time course of induced mental events (independent variable) provided a design matrix of experimental events to serve as supervised training so the model was able to learn to isolate diagnostic patterns of information in the feature set. The validity of this approach is confirmed by 3 independent measures: 1) decades of literature introducing empirical evidence for the very high correlation between eye behaviors and mental states; 2) carefully controlled experimental design and hardware calibration; 3) interactive feedback from the human participants to confirm the accuracy of the model inferences.

The first step was to induce and categorize basic mental states to establish a proof of concept for our method and to test the different modeling approaches and their independent abilities to predict mental states from a user's eye data. Subjects played a game to visually detect and discriminate objects with a mouse click, where rewards and penalties were delivered according to response accuracy. The stimuli were designed to discover contingencies and relationships among eye behaviors and how they change in response to changes in the environment during game play. Through the data collection process, several game features were integrated to induce three different types of mental states for model training and development. The first mental state was surprise and positive versus negative emotional valence, which was induced by delivery of either a large unexpected reward or penalty. The second state was the level of attentional engagement, or vigilance, which was induced by tasks that alternate between either highly focused attention or carefree distributed attention. The third state was the level of frustration versus satisfaction during game play, which was induced by the manipulation of game-play interference by randomly disabling or perturbing mouse click responses. Total control was maintained over the time course of the game-play, and hence, had a precise quantification of when mental events were induced during game play.

Eye data was acquired using a research-grade eye tracking system. The system comprised a comfortable frame of lens-less glasses, an infrared video camera attached to the frame and positioned near the right eye, and a full-color world facing camera (correlating eye behaviors to world events). The positioning of the hardware delivered optimal perspective of eye behavior without interfering with the user's central field of view, while capturing everything the user was looking at. This is a mobile eye-tracking setup with broad applications due to the cameras mounted to the frame, allowing for a stabilized real-time data stream relative to the head position, such that head movements did not introduce significant noise in the data, which is a common issue for desktop eye-tracking systems. Furthermore, the software utilized for acquiring and processing eye data was comparable to other more expensive and proprietary research-grade eye tracking systems (gaze accuracy=0.6 deg, precision=0.08 deg, latency=0.045 sec). The pupil was detected using the "dark pupil method".

During data collection, video frames and quantitative eye data (X, Y gaze position plus pupil diameter) were measured continuously and stored for additional post-hoc analysis. In addition, we developed a package of analysis software written in Python and Matlab to extract a host of different features from the data and controlled environmental manipulations. Our software estimated the time course of the following features:

Features: Eye Movement
Gaze location X
Gaze location Y
Saccade Rate
Saccade Peak Velocity
Fixation duration
Fixation entropy (spatial)
Gaze Deviation (Polar Angle)
Gaze Deviation (Eccentricity)
Re-Fixations
Smooth pursuit
Scan path (gaze trajectory over time)
Features: Pupillary System
Pupil diameter
Velocity (change in Pupil diameter)
Acceleration (change in velocity)
Constriction latency
Dilation duration
Spectral features
Iris muscle features
Features: Blinking
Blink rate
Blink Duration
Blink Latency
Partial blinks
Blink entropy (deviation from periodicity)
Eyeball area (squinting)

Many of these isolated features have been empirically shown to correlate and link quite strongly to various types of mental states (cognitive and emotional). Any single feature can provide probabilistic evidence for one mental state or another, however, the sequential and combinatorial patterns of these features taken together provide significantly more information to distinguish mental states at a finer-scale than any previous method. For instance, frustration may coincide with an increase in pupil diameter, but anger also causes pupil dilation. So how can frustration be distinguished from anger in this case? We found that frustration also happens to coincide with changes to other relevant features such as saccade rate due to increased eye movements, angular gaze deviations due to eye rolls, and other features related to an inward focus of attention, and/or high blink entropy due to irregular patterns of blinking. In contrast, the mental state of anger coincides with lower blink and saccade rates due to a very intense focus of intention on the object inducing the angry state. The purpose of behavioral data collection was to carefully induce particular mental states and the correlating eye features.

Participants played a game on the computer where the task was to identify target elements among distracters, and use the mouse to click on perceived targets. The targets appeared as basic luminance defined shapes (e.g., ellipses) that moved around the screen according to a simple algorithm that generated random movement patterns that appear animate (Lu, Thurman & Seitz, 2015). That is, the moving shapes appeared immediately (to most observers) as little bugs crawling on the computer screen, because the algorithm is designed with psychological principles of perceptual animacy to trigger animacy detectors in our visual system. In the natural environment, animate entities (bugs, animals, people, etc.) move according to volition which creates unpredictable turns, starts and stops, giving the appearance of intentional behavior. This type of stimulus is ideal because it is very engaging due to the fact that the stimuli appear animate and living things naturally capture and hold our attention.

The task is subdivided into discrete trials that last about 10 seconds each. The task will resemble a multiple object tracking task, in which target objects must be tracked amongst a group of distracting objects with identical appearance. At the start of the trial, a large number of objects (20-50) will be positioned randomly on the screen with uniform appearance. Then a small subset of the objects (5-10) will be indicated as targets by flashing in a distinct color such as gold. The targets will next change back to the color of the non-targets so that the targets must be remembered and tracked once they all start to move.

Task difficulty and attention were manipulated in several different ways. First, the parametric algorithm that generates animate movements was adjusted to make the elements move more quickly, or have more frequent and unpredictable turns, etc. This made the task very challenging because the subject not only had to track the various targets are over time, but also had to click accurately on the correct element to get points. When the elements moved rapidly every which way, the user had a lot of near-miss responses and accidentally clicked on non-targets, which led to frustration. Second, the ratio of targets to non-targets, as well as the total number of elements was manipulated to make the task easier or challenging, and modulated the user's cognitive load.

As an cross-measure, subjects were prompted to rate their subjective mood or feeling to confirm that the environmental manipulations had the desired effect of inducing frustration, positive surprise, reward, engagement, and cognitive load. The collected data was used as regressors for interpreting patterns in eye behaviors and for training the computational model to discriminate mental states.

Linear relationships between eye features and the environmental manipulations were determined through various statistical techniques. A general linear model was utilized to perform linear regression and compute beta weights to relate eye features to independent mental states (e.g., frustration or reward). The relationships among all of the eye features were examined to correlate independent or orthogonal features to increase the discrimination between similar mental states (e.g., enjoyment and engagement). As expected a strong relationship was found between some features and no relationship between others. The analyses provided general information for the eye features that were most informative, which combination of features were predictive of which mental state, and the specific features linked to specific mental states. A linear discriminant model or support vector machine was employed to determine the conservative baseline for how well eye feature data was able to predict and discriminate mental states.

The next stage of data inference utilized the proposed sophisticated computational modeling approach to discover non-linear patterns and relationships in the data, providing a strong basis for predicting mental states. First, a Bayesian Deep Belief Network (DBN) with supervised training was used. The network weights and connections modified (learned) based on the eye data, to find non-linear mappings between spatio-temporal patterns in the feature set (eye data) and the corresponding induced mental states. The computational model was trained on each observer individually so that the weights were learned optimally for that person. Performance was evaluated by using a model trained on one person's data to predict data from other people. Although the user model was optimized for discriminating mental states for the specific person, once carefully calibrated, there was sufficient commonalities between subjects, such that the model performed adequately on the other users.

The second set of stimuli were designed to induce and categorize additional mental states along with the previously categorized mental states by introducing more dynamic stimuli (video games). The data collected was utilized to further test the method and the computational model's ability to predict mental states from eye data. Users played two distinctly different games with a keyboard and a computer to solve puzzles of varying degrees of difficulty (game 1) or fight with a computerized opponent in a 2-D flat-planar environment (game 2). The stimuli were designed to discover contingencies and relationships among eye behaviors and how they change in response to changes in the environment during game play. Seven different types of mental states were elicited from the stimuli. The first mental state was the degree of cognitive load, induced by the difficulty of a puzzle without time-limits (game 1). The second state was the level of attentional engagement, or vigilance, which was directly related to the quantity of puzzles solved without time-limits (game 1) and the amount and type of moves landed on an opponent (game 2). The third state was the level of frustration versus satisfaction, which was a result of puzzle difficulty with a time-limit imposed (game 1) and opponent difficulty and complexity of a player's actions (game 2). The fourth state was fatigue/disengagement, which was induced by having a subject play easy puzzles without a time-limit (game 1) and play an opponent that doesn't move (game 2). The fifth state induced was surprise, which resulted from discovering the solution to a difficult puzzle (game 1) and learning a 'special' move to inflict significant damage on the opponent (game 2). The sixth mental state was the continuum from anticipation to anxiety, which resulted from the sequence of different computerized opponent conditions (transitions from or to hard opponent conditions) in game 2. The seventh state was the continuum from stressed to relaxed, which resulted from being attacked excessively or playing a neutral opponent, respectively (game 2). In contrast to the previous stimuli, the time course of the environmental manipulations were not controlled, instead, the time course of the games was recorded along with the eye behaviors and game actions, which led to a precise quantification of when mental events were induced during game play.

Users played two different games on the computer with a keyboard, where the task was simply to perform their best. The eye behaviors were collected and timestamped along with game sequences and user actions to provide a complete data set corresponding eye behaviors to game conditions and actions performed. The subject received real-time feedback of performance in terms of points scored in game 1 and both energy bars (opponent and subject) in game 2.

In game 1, the subjects needed to think through the various puzzles with and without time-limits. Each puzzle served as a block of data either with or without a time-limit and a randomly assigned difficulty level (easy, medium, and difficult).

In game 2, the users played a series of matches with a computerized opponent. The computerized opponent was randomly assigned to 1 of 3 conditions (easy, hard, and neutral). In the easy and hard conditions, the user was provided real-time feedback of their performance from the energy bars of both the user and the computerized opponent. The energy bars were deterministically decreased when a punch, kick, or special move are 'landed' on either player (some moves decreased an opponent's energy more than others). In the neutral condition, the computerized opponent did not move, the user did not receive feedback, and there was no clear objective. Whereas, in the easy and hard conditions, the objective was clear, the user had to defeat the computerized opponent. A defeat was either determined by the player (user or opponent) with the least amount of energy (quantitative comparison) at the end of the match, or the player that had their entire energy bar drained by receiving too many punches, kicks, and/or special moves.

Between each game, users were prompted to rate their subjective mood or feeling to help quantify and confirm that the environmental manipulations had the desired effect. The data was used as regressors for interpreting the patterns in measured eye data and for improvements to the computational model's ability to discriminate user mental states.

Several of the eye features contained relevant information in their time course to predict changes in emotional state induced by different game environments. For example, pupil diameter changes correlated with the general task structure (pupil dilates during game-play versus rest periods), but also with rewarding feedback, surprises, anticipation/anxiety, and other emotional responses linked to the autonomic nervous system.

In general, the second set of stimuli allowed the exploration of the feature set in greater depth and in a more natural environment showing that eye behaviors are consistent across the dramatically different stimuli. The computational modeling approach for predicting mental state from the large set of eye data set the stage for additional environmental manipulations with more sophisticated stimuli to explore different categories of mental states and emotion through more complex video games and/or viewing of movies and other engaging multimedia. The secondary set of stimuli push the boundary to discover how fine-grained the computational model will discriminate human thoughts, feelings and complex mental states.

In a future set of experiments (Phase II), we intend on utilizing a completely naturalistic environment with free-form social interactions. We will provide our participants with a fully mobile set of hardware and ask them to go about their day. We expect to record eye behaviors in situations like ordering a cup of coffee or sitting through a lecture in a classroom. However, due to the highly exploratory and less controlled nature of these experiments, we first need to confirm that the Bayesian deep belief network is fully capable of determining the mental and emotional states of an individual in the laboratory with a high degree of accuracy. The experiments performed "in the wild" will have a human subject wear the device and occasionally receive a 'ping' (via text message, email, or customized phone application) on their smart phone at random intervals to either confirm or decline if the Bayesian model was accurately predicting their current mental state. Over time the subject will have supplied minutes or perhaps hours of data to relate to a broader range of complex mental states encoded via self-report in real time and real life situations.

In addition, we will conduct functional magnetic resonance imaging (fMRI) experiments to conclusively determine the neural correlates of the displayed eye behaviors. Furthermore, we will investigate participants' iris muscles and their dynamics to uncover a completely new method for determining a person's mental state, with implications towards their health. Although there is less literature on dynamic features of the human iris (Gonzaga & Da Costa, 2009; Larsson, Pedersen, & Stattin, 2007; Neuhuber & Schrödl, 2011; Pintor, 2010), we hypothesize that patterns of the human iris could provide further information to discriminate mental states and a person's health. As reviewed previously, the iris muscles are controlled by the autonomic nervous system, and there are several hundred individual muscles in the iris (Pintor, 2010).

Phase II will nicely complement the methods used in the laboratory approach (Phase I) and has the potential to help discover a richer set of relationships between more fine-grained mental states and eye features, along with potential dynamics associated with social interaction, iris muscles, and brain activity.

FIG. 1 is a simplified schematic of the present invention showing a user 10 wearing a pair glasses 12 with an infrared camera 14 aimed as the user's eye 22 and a forward looking camera 16 taking in the environmental view that the user would be perceiving. The pair of glasses 12 may or may not have any lens attached. If a person wears a prescription pair of glasses, the glasses may have such prescription lenses included. However, it is simplified if the user does not require glasses such that the infrared camera gets an unobstructed view of the user's eye 22. The pair of glasses 12 can then send the recorded information via a wireless link 18 to a computing device 20, or be hardwired (not shown). The computing device 20 can be a desktop computer, a laptop, a smart device capable of being transported easily. As can be seen by those skilled in the art the computing device can take the size and shape of many forms. It will also be understood that the pair of glasses 12 could instead be a head gear, a hat, or various types of fitments that would properly locate the infrared camera 14 and the forward/outward looking camera 16 upon the user 10. It is understood that the pair of glasses 12 would also have enough computational logic and chips to be able to record the data and then transmit or send the data to the computing device 20. This means the glasses 12 would have a separate power source (battery) such that the user could simply put on the pair of glasses 12 and be able to record the necessary information. The battery 24 could be installed in the ear portion or anywhere as part of the glasses 12. Small batteries like those found in hearing aids and the like could be utilized.

In many of the embodiments taught herein the camera 14 is an infrared camera. However, in other embodiments this camera does not have to be infrared but rather could be a regular camera that records in either black and white or in color. It is understood by those skilled in the art that different types of cameras could be used as taught herein.

Furthermore, in many of the embodiments shown herein the cameras 14 and 16 are integrated into a pair of glasses, a hat, head gear or the like. It will be understood that the cameras 14 and 16 can be together in a single unit or separate cameras. Furthermore, it is understood that two separate cameras could be used that are simply set up in the appropriate positions to record the necessary information. In yet another embodiment, a smart phone could be used to record the necessary videos as many smart phones today have a forward looking camera and a rear looking camera. For example, the forward looking camera could be capturing the world view of the user while the rear facing camera could be recording various eye movements.

The invention taught and disclosed herein can have many applications for use in the future. Once the relationship between eye movements are discovered and better understood, the present invention can not only identify such relationships, but be used to detect the emotional states of various persons of interest. For example, various government agencies could use the present invention to interview possible criminal suspects in law enforcement purposes or be used by the immigration departments to help interview various foreigner travelers or immigrants. Psychologists and therapists could use the present invention to better understand the mental states and emotions of their patients to then administer better therapy and counseling. Using one's smart device with both cameras, the user could self-diagnose their mental states and emotions to help in getting better clarity of mental health and overall wellbeing. Emotional states can also be used in a video game setting or virtual reality setting where the game would change what it displayed to the user based on the user's emotional state. As can be see, the present invention taught herein can be used in a multitude of ways that could benefit individuals and society as a whole.

As the technology develops and advances from further understandings of the relationships between various eye movements and emotional states, it is possible to remove the forward looking camera and only rely upon the camera facing the eye for emotional state determination. This could simplify the requirement for two cameras down to just one.

Although several embodiments have been described in detail for purposes of illustration, various modifications may be made to each without departing from the scope and spirit of the invention. Accordingly, the invention is not to be limited, except as by the appended claims.

What is claimed is:

1. A method of discovering relationships between eye movements and emotional responses of a user, the method comprising the steps of:
    engaging the user in a plurality of tasks, each task comprising a computer video game requiring a user's input, and each task of the plurality of tasks configured to elicit a predicted specific emotional response from the user;
    varying an environment of the computer video game during game play to elicit the predicted specific emotional response from the user;
    providing a first camera filming at least one eye of the user;
    recording a first time series of eye movements by the user with the first camera;
    providing a second camera filming an outward looking view of the user;
    recording a second time series of outward events perceived by the user with the second camera;
    wherein the first time series and second time series are taken at the same time;
    sending the first time series and second time series to a computing device;
    comparing, by the computing device, the eye movements from the first time series and the outward events from the second time series;
    gathering a feedback from the user of an actual specific emotional response during at least one task of the plurality of tasks;
    verifying with feedback from the user whether the actual specific emotional response during at least one of the plurality of tasks was the same as the predicted specific emotional response; and
    identifying, by the computing device, at least one relationship between eye movements that correlate to the actual specific emotional response.

2. The method of claim 1, wherein the eye movements comprise X gaze location, Y gaze location, saccade rate, saccade peak velocity, fixation duration, fixation entropy, gaze deviation of polar angle, gaze deviation of eccentricity, re-fixations, smooth pursuits and scan path.

3. The method of claim 1, wherein the eye movements comprise a change in the pupillary system which includes pupil diameter, velocity of the change in the pupil diameter, acceleration of the change in the pupil diameter, constriction latency, dilation duration, spectral features and iris muscle features.

4. The method of claim 1, wherein the eye movements comprise a change in blinking which includes blink rate, blink duration, blink latency, partial blinks, blink entropy and squinting.

5. The method of claim 1, wherein at least one task of the plurality of tasks comprises a task configured to deliver a large unexpected reward or penalty, wherein the predicted specific emotional response comprises surprise.

6. The method of claim 1, wherein at least one task of the plurality of tasks comprises a task configured to alternate between highly focused attention or carefree distributed attention, wherein the predicted specific emotional response comprises vigilance.

7. The method of claim 1, wherein at least one task of the plurality of tasks comprises a task configured to randomly disable mouse click responses when the user was interacting with game-play on a computer, wherein the predicted specific emotional response comprises frustration and/or satisfaction.

8. The method of claim 1, wherein at least one task of the plurality of tasks comprises a task configured to vary the difficulty of puzzle between easy and hard, wherein the predicted specific emotional response comprises a corresponding low to high degree of cognitive load.

9. The method of claim 1, wherein at least one task of the plurality of tasks comprises a task configured to change an opponent condition in a subsequent task, wherein the predicted specific emotional response comprises anxiety.

10. The method of claim 1, wherein at least one task of the plurality of tasks comprises a task configured to change the level of attack on the user, wherein the predicted specific emotional response comprises stress.

11. The method of claim 1, wherein the first camera and the second camera are integrated into a pair of glasses to be worn by the user, wherein the pair of glasses may or may not have lenses.

12. The method of claim 1, wherein the plurality of tasks comprise computer games utilizing a computer mouse, joystick and/or keyboard.

13. The method of claim 1, wherein each task of the plurality of tasks comprises a set time period.

14. The method of claim 1, wherein each task of the plurality of tasks comprises a set time period of 10 seconds.

15. The method of claim 1, wherein the step of identifying, by the computing device, relationships between eye movements that correlate to the outwards events comprises linear regression computing beta weights to relate eye movements to emotional responses.

16. The method of claim 1, wherein the step of identifying, by the computing device, relationships between eye movements that correlate to the outwards events comprises identifying non-linear patterns using bayesian deep belief networks.

17. The method of claim 1, wherein the first camera is an infrared camera.

18. The method of claim 1, wherein the second camera is a full-color camera.

19. A method of discovering relationships between eye movements and emotional responses of a user, the method comprising the steps of:
engaging the user in a plurality of tasks, each task comprising a computer video game requiring a user's input, and each task of the plurality of tasks configured to elicit a predicted specific emotional response from the user;
varying an environment of the computer video game during game play to elicit the predicted specific emotional response from the user;
providing a first camera filming at least one eye of the user;
recording a first time series of eye movements by the user with the first camera;
providing a second camera filming an outward looking view of the user;
recording a second time series of outward events perceived by the user with the second camera;
wherein the first time series and second time series are taken at the same time;
sending the first time series and second time series to a computing device;
comparing, by the computing device, the eye movements from the first time series and the outward events from the second time series;
identifying, by the computing device, at least one relationship between eye movements that correlate to an actual specific emotional response of the user when engaging in the at least one of the plurality of tasks configured to elicit the predicted specific emotional response.

20. A method of discovering relationships between eye movements and emotional responses of a user, the method comprising the steps of:
engaging the user in a naturalistic environment with free-form social interactions;
providing a first camera filming at least one eye of the user;
recording a first time series of eye movements by the user with the first camera;
providing a second camera filming an outward looking view of the user;
recording a second time series of outward events perceived by the user with the second camera;
wherein the first time series and second time series are taken at the same time;
wherein the first camera and the second camera are integrated into a pair of glasses to be worn by the user, wherein the pair of glasses may or may not have lenses;
sending the first time series and second time series to a computing device;
comparing, by the computing device, the eye movements from the first time series and the outward events from the second time series;
identifying, by the computing device, at least one specific interaction from the free-form social interactions; and
identifying, by the computing device, at least one relationship between eye movements that correlate to a predicted specific emotional response of the user when engaging in the at least one specific interaction from the free-form social interactions.

21. The method of claim 20, including the step of gathering a feedback from the user of an actual specific emotional response during the at least one specific interaction from the free-form social interactions, wherein the step of gathering comprises a text message.

22. The method of claim 21, including the step of verifying with the feedback from the user whether the actual specific emotional response during the at least one specific interaction from the free-form social interaction was the same as the predicted specific emotional response.

* * * * *